(12) United States Patent
Kinker et al.

(10) Patent No.: US 8,021,885 B2
(45) Date of Patent: Sep. 20, 2011

(54) METHOD FOR THE DETERMINATION OF THE OXIDATIVE STABILITY OF A LUBRICATING FLUID

(75) Inventors: Bernard Kinker, Kintnersville, PA (US); Raymond Romaszewski, Riegelsville, PA (US)

(73) Assignee: Evonik Rohmax Additives GmbH, Darmstadt (DE)

( * ) Notice: Subject to any disclaimer, the term of this patent is extended or adjusted under 35 U.S.C. 154(b) by 1103 days.

(21) Appl. No.: 11/545,421

(22) Filed: Oct. 11, 2006

(65) Prior Publication Data

US 2008/0090296 A1    Apr. 17, 2008

(51) Int. Cl.
*G01N 33/03* (2006.01)

(52) U.S. Cl. .................. 436/60; 436/155; 436/159

(58) Field of Classification Search ............ 436/60, 436/155, 159
See application file for complete search history.

(56) References Cited

U.S. PATENT DOCUMENTS

| | | | | |
|---|---|---|---|---|
| 4,745,070 A | * | 5/1988 | Korcek et al. | 436/60 |
| 5,401,661 A | * | 3/1995 | Florkowski et al. | 436/6 |
| 5,501,714 A | * | 3/1996 | Valentine et al. | 44/358 |
| 2005/0181512 A1 | * | 8/2005 | Wollenberg | 436/60 |

* cited by examiner

*Primary Examiner* — Vickie Kim
*Assistant Examiner* — Dwan A Gerido
(74) *Attorney, Agent, or Firm* — Oblon, Spivak, McClelland, Maier & Neustadt, L.L.P.

(57) ABSTRACT

The present invention concerns a method for the determination of the oxidative stability of a lubricating fluid, comprising the steps of:

- introducing a sample of the lubricating fluid under test in an reaction cell;
- introducing catalytic amounts of a catalyst to the reaction cell;
- heating the cell to the oxidation temperature of the lubricating fluid and maintaining this temperature;
- delivering oxygen containing gas at constant flow rate through the cell over the course of the reaction;
- delivering a gas comprising nitrogen dioxide at a constant flow rate through the cell for a specified time;
- applying and maintaining a specified vacuum on the reaction cell;
- allowing the mixture to react for a specified time;
- measuring the viscosity of the oxidized lubricating fluid.

Additionally, the present invention describes an apparatus for the determination of the oxidative stability of a lubricating fluid.

16 Claims, No Drawings

METHOD FOR THE DETERMINATION OF THE OXIDATIVE STABILITY OF A LUBRICATING FLUID

The present invention relates to a method for the determination of the oxidative stability of a lubricating fluid.

There are several ASTM engine Sequence tests which must be run to achieve passing results in order to certify candidate engine lubricant formulations to meet API (American Petroleum Institute) and ILSAC (International Lubricant Standardization and Approval Committee) standards. These tests are very expensive and time consuming. Therefore, it is desirable to add laboratory bench to the lubricant certification process is where possible in order to control the cost escalation and complexity of new category development.

There are examples of attempts to develop meaningful tests such as those cited below. But, none of the following examples have been utilized in any engine oil specification.

For example, Glenn A. Mazzamaro, "Using Laboratory Tests to Predict Oxidation in Today's Engines", Lubricating Oil, Vol. 19, No. 6, 2004, p 6-11, describes a special oxidation test comprising a pre-aging step. Oxygen gags is used for the oxidation test of the lubricant. Furthermore, Mazzamaro reviews various known bench oxidation tests and then focuses on the 'VIT' (viscosity increase test) referenced in a 1994 publication as a screening test for Sequence IIIE. The Sequence IIIE test was developed in 1988 and has been replaced by the more severe Sequence IIIE (2001) and later by the even more severe Sequence IIIG (2004). However, the aging according to the Sequence IIIG or IIIGA is not mentioned in the Mazzamaro document. Furthermore, as mentioned above, oxygen gas is used to oxidize the lubricating fluid.

A typical oxidation test as reviewed by Mazzamaro is mentioned in S. H. Roby, "Development of a Bench Test to Predict Oxidative Viscosity Thickening in the Sequence IIIG Engine Test", SAE Technical Paper Series 2004-01-2985. Oxygen gas is used for the oxidation test of the lubricant. The Roby document does not mention the use of nitrogen oxide. Furthermore, the correlation of the Roby test with the Sequence IIIG Engine Test is poor.

The use of nitrogen oxide gas to determine the oxidative stability of lubricant components is mentioned by DeBarros Bouchet (M. I. DeBarros Bouchet et al., "Mechanism of the $MoS_2$ formation by MoDTC in the presence of ZnDTP: effect of oxidative degradation", Wear, (2005) 1643-1650) and J. M. Martin (J. M. Martin et al., "Effect of oxidative degradation on the mechanism of friction reduction by MoDTC", Boundary and Mixed Lubrication: Science and Applications, D. Dowson et al. (Editors) Elsevier Science 2002). However, the documents of DeBarros Bouchet and Martin relate to the oxidative degradation of MoDTC and ultimate loss of friction modification and thus fuel economy improvement. While the experimentation utilizes nitrogen oxide as a 'blow by gas', the work does not relate to prediction of used oil rheology either at higher or cold temperatures nor to Sequence IIIG engine testing. In fact, it relates to a completely different topic, namely fuel economy rather than engine oil robustness as predicted by used oil rheology. In practical terms this translates to long lubricant life which corresponds to long drain intervals.

Taking into consideration the prior art, it is an object of this invention to provide a simple and inexpensive method for the determination of the oxidative stability of a lubricating fluid. Furthermore, it is an object of the present invention to provide a method for the determination of the oxidative stability of a lubricating fluid so as to predict the Theological results of a Sequence IIIG engine test.

These as well as other not explicitly mentioned objectives, which can easily be derived or developed from the introductory part, are achieved by the method for the determination of the oxidative stability of a lubricating fluid according to present claim 1. Expedient modifications of the method in accordance with the invention are described in the dependent claims.

The method for the determination of the oxidative stability of a lubricating fluid provides an unexpected improvement in the prediction of the rheological results of a Sequence IIIG Engine test. The method of the present invention provides a simple and inexpensive process to determine the results of a Sequence IIIG Engine test.

At the same time a number of other advantages can be achieved through the method in accordance with the invention. Among these are:

The method can be performed in a relatively short time.

The method to determine the oxidative stability of a lubricating fluid needs only a very small amount of lubricating fluid.

The method according to the present invention is less complex than the Sequence IIIG engine aging procedure. Consequently, the method can be performed in semi-automated manner and without highly skilled personnel.

The present invention provides a method for the determination of the oxidative stability of a lubricating fluid, comprising the steps of:

introducing a sample of the lubricating fluid under test in an reaction cell;

introducing catalytic amounts of a catalyst to the reaction cell;

heating the cell to the oxidation temperature of the lubricating fluid and maintaining this temperature;

delivering a gas comprising oxygen at constant flow rate through the cell over the course of the reaction;

delivering a gas comprising nitrogen dioxide at a constant flow rate through the cell for a specified time;

applying and maintaining a specified vacuum on the reaction cell;

allowing the mixture to react for a specified time;

measuring the viscosity of the oxidized lubricating fluid.

The reaction cell used to determine the oxidative stability of the lubricating fluid is known in the art. These cells can be made of any material being stable under the test conditions. Useful materials are e.g. glass, special plastics, metals, or stainless steel. Additionally, the oxidation cell is equipped with a means for agitating or stirring the lubricating fluid.

For determination of the oxidative stability of a lubricating fluid, the cell is heated to the desired reaction temperature for the lubricating fluid. The oxidation temperature can be selected to achieve the desired oxidative severity. Preferably, the oxidation temperature is in the range of 140° C. to 220° C., more preferably 150° C. to 200° C. and most preferably 160° C. to 180° C. According to a preferred embodiment, an oxidation temperature of about 170° C. can be used. The heating can be started after the sample has been introduced into the reaction cell.

According to a preferred embodiment of the present invention, the heating of the cell can be performed under a reduced pressure. The reduced pressure can be applied before and/or during the heating. Preferably, the reduced pressure is 0.1 MPa or less, more preferably 0.08 MPa or loss. According to a preferred embodiment, the reduced pressure is in the range of 0.05 to 0.07 MPa, more preferably in the range of 0.057 to 0.064 MPa and most preferably 0.061 to 0.063 MPa.

In order to oxidize the lubricating fluid, a catalyst can be used. E.g., the catalyst can be mixed with the lubricating fluid before the sample is introduced in the reaction cell. Preferably, the catalyst comprises a metal, e.g. copper, iron. In a preferred embodiment iron ferrocene is the desired catalyst as it is a soluble liquid and metal from engine wear.

Preferably, the amount of the metal catalyst can be in the range of 5 to 25 ppm, more to preferably in the range 10 to 20 ppm, based on the total weight of the sample to be oxidized.

The method of the present invention includes a step of delivering a gas comprising oxygen at constant flow rate through the cell over the course of the reaction. Usually every gas comprising an effective amount of oxygen can be used. According to a preferred embodiment of the present invention, a gas comprising at least 5% by volume, more preferably at least 10% by volume of oxygen is used. Preferably, the oxygen containing gas comprises 15 to 30% by volume, more preferably 20 to 22% by volume oxygen. Furthermore, the oxygen containing gas can comprise additional gases, like inert gases, e.g. nitrogen ($N_2$) and noble gases, e.g. argon, neon, helium. Preferably, dry air can be used as an oxygen containing gas.

The oxygen containing gas is delivered to the cell at a constant flow rate. Constant flow rate means that the amount of oxygen containing gas in the oxidation cell is kept essentially at a constant value over the course of the reaction. However, small changes having no significant influence to the test result should be included to the meaning of the expression "constant flow rate", Preferably, the flow rate of the oxygen containing gas is in the range of 120 to 240 milliliters per minute, more preferably 150 to 200 milliliters per minute and more preferably in the range of 180 to 190 milliliters per minute throughout the reaction, based on a reaction cell volume of about 1 liter.

According to the method of the present invention, a gas comprising nitrogen dioxide is delivered at a constant flow rate through the cell for a specified time to provide a vigorous gaseous oxidation catalyst. The gas comprising nitrogen dioxide comprises preferably at least 1% by weight, more preferably 50% by weight or more and more preferably 90% by weight or more nitrogen dioxide. The person skilled in the art knows that nitrogen dioxide is usually in equilibrium with a mixture of nitrogen oxide and oxygen. Therefore, also an appropriate mixture can be added to the reaction cell. Furthermore, the nitrogen dioxide containing gas can comprise additional gases, like inert gases, e.g. nitrogen ($N_2$) and noble gases, e.g. argon, neon, helium.

The gas comprising nitrogen dioxide is delivered after heat up and then continues through the remaining heating of the reaction cell at the reaction temperature for a specified time. 'Remaining heating' means that the cell has reached the reaction temperature and is maintained at the desired temperature. Preferably, the oxidation cell reaches the oxidation temperature within 45 minutes, more preferably within 30 minutes.

In order to oxidize the lubricating fluid to determine the fluid's oxidative stability, a gas comprising nitrogen dioxide gas is delivered to the cell at a constant flow rate. Constant flow rate means that the amount of nitrogen dioxide containing gas in the oxidation cell is kept essentially at a constant value for a specified time. However, small changes having no significant influence to the test result should be included to the meaning of the expression "constant flow rate". Preferably, the flow rate of the gas comprising nitrogen dioxide is in the range of 0.14 to 0.2 milliliters per hour, more preferably in the range of 0.15 to 0.18 milliliters per hour, based on a reaction cell volume of about 1 liter. The gas comprising nitrogen dioxide is delivered for a specified time. Preferably, the specified time for delivering the gas comprising nitrogen dioxide is in the range of 5 to 30 hours, more preferably in the range of 8 to 15 hours and more preferably in the range of 11 to 13 hours.

Preferably, the total amount of nitrogen dioxide gas delivered to the reaction cell is in the range of 0.0043 to 0.0063 mol per gram of the lubricating fluid, more preferably in the range of 0.004697 to 0.00564 mol per gram of the lubricating fluid.

Preferably, the total amount of nitrogen dioxide delivered to the reaction cell is in the range of 0.1 to 5% by weight, more preferably 0.5 to 3% by weight, more preferably in to the range of 1 to 2% by weight, and more preferably in the range of 1.4 to 1.5% by weight based on the total amount of lubricating fluid at the start of the test.

According to a preferred embodiment of the present invention, the delivering of the gas to the cell can be performed under a reduced pressure. Preferably, the reduced pressure is 0.1 MPa or less, more preferably 0.08 MPa or less. According to a preferred embodiment, the reduced pressure is in the range of 0.05 to 0.07 MPa, more preferably in the range of 0.057 to 0.064 MPa and most preferably 0.061 to 0.063 MPa.

The gas comprising nitrogen dioxide and the oxygen containing gas can be provided separately or as a mixture to the reaction cell. Preferably, both gases are mixed in order to achieve a good distribution of the nitrogen dioxide containing gas.

The present method includes a step of applying and maintaining a specified vacuum on the reaction cell. Therefore, the oxidation reaction is performed under a reduced pressure. Preferably, the reduced pressure is 0.1 MPa or less, more preferably 0.08 MPa or less. According to a preferred embodiment, the reduced pressure is in the range of 0.05 to 0.07 MPa, more preferably in the range of 0.057 to 0.064 MPa and most preferably 0.061 to 0.063 MPa.

Astonishingly, the engine operation can be mimicked by applying a reduced pressure Such step is not suggested by any other prior art. Surprisingly, a detailed analysis revealed that the Sequence IIIG actually volatilizes about 40 to 50% of the lubricating fluid that is charged to the engine. That is, at the end of the 100 hour Sequence IIIG procedure only 50 to 60% of the lubricating fluid remains in the engine. The present invention also removes about 40 to 50% of the lubricating fluid charge just as the Sequence IIIG does. No other bench oxidative conditioning procedure in the lubricant testing area uses a vacuum and no other bench oxidative procedure can duplicate the results of the engine procedure Sequence IIIG. The results of the present method were not foreseeable for the person skilled in the art.

The present inventors have surprisingly found that the less viscous, volatile components have an unfavorable effect with regard to the duplication of the rheology of used oil from the Sequence IIIG engine procedure.

The oxidation of the lubricating fluid in the reaction cell is performed for a specified time. Preferably, the specified time is in the range of 30 to 50 hours, more preferably 38 to 42 hours.

Preferably, the lubricating fluid can be stirred and/or agitated during the delivering of the gases to the reaction cell and/or the heating of the lubricating fluid in the oxidation cell and the application of vacuum.

In order to determine the oxidative stability of the lubricating fluid, the viscosity of the oxidized lubricating fluid is measured. Preferably, the Mn-Rotary Viscosity of the lubricating fluid is measured according to ASTM D 4684 and the kinematic viscosity at 40° C. of the lubricating fluid is measured according to ASTM D 445. These rheological properties can be measured before and after the oxidation has been performed. Preferably, the lubricating fluid is oxidized by delivery of the nitrogen dioxide and oxygen containing gases along with a catalyst at the specified temperature under vacuum in the reaction cell. The lubricating fluid obtained at the end of the oxidation reaction and volatilization period is considered as the oxidized lubricating fluid. Preferably, the change induced by the oxidation and volatilization in MRV viscosity at cold temperature and kinematic viscosity higher temperatures such as 40° C. of the lubricating fluid is determined.

The method of the present invention can be performed in the analysis of all kinds of lubricating fluids. These fluids include engine lubricants in particular but might also include other functional fluids such as transmission fluids or even hydraulic fluids. These fluids are well known in the art and are described, e.g., in Uilmann's Encyclopedia of Industrial Chemistry, 5th Edition on CD-ROM, 1997, e.g. under the entry "lubricants and related products."

Preferred lubricant fluids are classified by the American Petroleum Institute (API), by the Society of Automotive Engineers (SAE) and by the International Lubricant Standardization and Approval Committee (ILSAC).

Lubricant base stocks are categorized into five groups by the API. Motor oils are further categorized by their API service class. The API service classes have two general classifications: S for Service (typical passenger cars and light trucks using gasoline engines) and C for commercial applications (typical diesel equipment). The latest API service standard designation is SM for gasoline engines.

The latest standard according to ILSAC, GF-4 was approved in 2004. The Sequence IIIG involves running a 1996/1997 V-6 GM 3800 CC Series II engine 3 at 125 horsepower, 3600 rpm, and 150° C. oil temperature for 100 hours. The test is divided into five 20 hour segments each followed by sampling.

The Sequence IIIGA include tests concerning sludge and varnish deposition, oil consumption, and engine wear; and oil thickening at 40° C. (KV). Furthermore the Sequence IIIGA include the determination of oil thickening at pumping temperature of original SAE W grade or at 5° C. warmer (MRV). The allowed maximum kinematic viscosity increase at 40° C. is 150%. The low temperature viscosity of the aged oil is determined according to ASTM D 4684 (MRV TP-1). The MRV TP-1 viscosity of the end of test sample must meet the requirements of the original grade or the next higher grade. A pertinent reference is ASFM D4485-03a "Standard Specification for Performance of Engine Oils".

The Sequence IIIG test is about 50% more difficult than the previous IIIF test, used in GF-3 and API SL oils (see e.g. D. McFall, Lubes and Greases Magazine, January 2005, p. 2.3). The Sequence IIIF test is described in ASTM D 6984-5a, "Standard Test method for valuation of Automotive Engine Oils in the Sequenec IIIF, Spark-Ignition Engine".

Preferred lubricating fluids comprise at least a mineral oil and/or a synthetic oil and/or a biologically sourced oil.

Mineral oils are well known in the art and commercially available. They are in general obtained from petroleum or crude oil by distillation and/or refining and optionally additional purification and processing methods, especially the higher-boiling fractions of crude oil or petroleum fall under the concept of mineral oil. In general, the boiling point of the mineral oil is higher than 200° C., preferably higher than 300° C., at 5000 Pa. Preparation by low temperature distillation of shale oil, coking of hard coal, distillation of lignite under exclusion of air as well as hydrogenation of hard coal or lignite is likewise possible. Preferably, the lubricating fluid is based on mineral oil from API Group I, II, and/or III or mixtures of these.

Biologically sourced oils can also be produced from raw materials of plant origin (for example jojoba, rapeseed (canola), sunflower, and soybean oil) or animal origin (for example tallow or neatfoots oil). Accordingly, mineral oils exhibit different amounts of aromatic, cyclic, branched and linear hydrocarbons, in each case according to origin.

Synthetic oils are, among other substances, polyalphaolefins, organic esters like carboxylic esters and phosphate esters; organic ethers like silicone oils and polyalkylene glycol; and synthetic hydrocarbons, especially polyolefins. They are for the most part somewhat more expensive than the mineral oils, but they have advantages with regard to performance. For an explanation reference is made to the 5 API classes of lease oil types (API: American Petroleum Institute).

The lubricating fluid may comprise further additives well known in the art such as viscosity index improvers, antioxidants, anti-wear agents, corrosion inhibitors, detergents, dispersants, EP additives, defoamers, friction reducing agents, pour point depressants, dyes, odorants and/or demulsifiers. These additives are used in conventional amounts. Usually the lubricating fluids contain 0 to 50% by weight, preferably 0.1 to 20% by weight and more preferably 0.2 to 10% by weight additives.

A preferred apparatus to perform the present invention comprises a reaction cell, e.g. a one liter reaction cell, with an integral heating element for containing a sample of the lubricant;

means for heating the cell to the oxidation temperature of the lubricant;

means for mixing the lubricant;

means for bubbling a gas comprising oxygen at a constant flow rate in subsurface feed through the cell;

means for bubbling nitrogen dioxide gas at a constant flow rate in subsurface feed through the cell for a specified time;

means for reducing pressure of the cell at a constant flow rate and collecting the resulting distillate;

means of introducing catalytic amounts of catalyst, e.g. iron ferrocene, to the lubricant;

means of measuring nitrogen dioxide liquid;

means of measuring and controlling elapsed time of the reaction.

According to a preferred embodiment, the reaction cell with an integral heating element may include a stainless steel flat head with various threaded ports; a packing gland housing for providing a seal around the agitator shaft; rods to support the head and cell to a laboratory hood framework and a clamp to connect the cell to the head.

Preferably, the heating means may include a temperature-controller with an on/off algorithm for maintaining reaction temperature; a J-thermocouple sensor; and a voltage controller for maintaining low voltage to cell heating element.

According to a further preferred embodiment, the mixing means may include an electric motor capable of maintaining constant revolutions per minute; and a stainless steel 45° pitched blade stirrer, preferably having approximate diameter 65 mm, height 30 mm, thickness 1.5 mm and preferably attached to a 8 mm rod.

The bubbling oxygen gas means may preferably include a gas supply capable of maintaining constant flow; a flow meter for measuring the flow rate of the oxygen containing gas; a gas drying jar for filtering moisture from the oxygen containing gas; and a high temperature tube positioned to bottom of cell.

Preferably, the bubbling nitrogen dioxide gas means may include a glass graduated tube to measure the flow rate of nitrogen dioxide and a stainless steel metering valve to maintain a constant flow of nitrogen dioxide to the oxygen gas bubbling tube.

According to a preferred embodiment of the reduced pressure at a constant flow rate and distillate collection means may include a vacuum pump with sufficient capacity to achieve a constant flow at reduced pressure with a closed cell; a flow meter to measure the flow rate of the oxygen containing gas; a stainless steel needle valve to control the flow rate of the oxygen containing gas; and a condenser of correct size to limit pressure drop and collect distillate and means of recovering the distillate.

Preferably, means for introducing a catalyst may include analytical balance capable of weighing to the nearest 0.0001 gram.

Measuring nitrogen dioxide liquid means may prefer ably include a stainless steel ball valve to vent system when apparatus is disconnected; a stainless steel needle valve to control the flow of liquid nitrogen dioxide; a graduated glass tube, more preferably a 12 milliliter graduated glass tube; a 3-way plug valve to direct liquid nitrogen dioxide to tube or nitrogen dioxide gas to cell; and a metering pump to evacuate nitrogen dioxide from graduated glass tube.

The measuring and controlling elapsed time of the reaction means may preferably include a sixty hour count down time controller.

The present invention provides a new and inventive method to predict the changes in viscosity as determined after the Sequence IIIG Engine test. The Sequence IIIG Engine test is well known in the art (see e.g. ILSAC GF-4).

The correlations of the results of a Sequence IIIG Engine test with the results of the present method are astonishingly good.

The invention is illustrated in more detail below by example 1 without intending to limit the invention to that example.

EXAMPLE 1

A closed reaction cell for oxidative conditions has been prepared by setting the velocity of flow to about 56.66 liter per minute at a given vacuum target of about 0.061 MPa (face velocity created by a vacuum pressure of 0.061 MPa), once set; the cell has been reopened. The valve configuration to collect the liquid nitrogen dioxide from the lecture bottle to the graduated glass tube has been set. The valve configuration has been reset back to reactor for nitrogen dioxide gas delivery. In a glass beaker 200.0 grams of the formulated oil as mentioned in the following tables with 15 ppm iron catalyst (Iron ferrocene) based on oil weight has been weighted and mixed in beaker. The mix of oil and catalyst has been charged to the reaction cell, agitation has been started and the reaction cell has been closed. The cell has been brought to reduced pressure (already set), the air flow has been adjusted to about 185 milliliters per minute and timer has been set to the specified reaction time of about 40 hours. The temperature controller has been set to heat the reaction to 170° Celsius and the nitrogen dioxide feed has been adjusted to deliver gas over 12 hours at a flow rate of about 0.16 milliliters per hour. The total weight of nitrogen dioxide delivered to the cell was 2.886 grams (1.443% by weight).

The test results of ASTM Reference Oils 438, 435 and 434 are mentioned in the following tables I, II and III,

TABLE I

Comparison of MRV TP-1 viscosity and Kinematic viscosity increase @ 40° Celsius from the Sequence IIIG and Laboratory Reactor Aged Oils

| Sample | % Viscosity Increase @ 40° Celsius | MRV TP-1 Ys, Pa/Viscosity, cP |
|---|---|---|
| ASTM Oil 438 Sequence IIIG Engine | | |
| 1 | 88.0 | No/16,700 |
| 2 | 90.0 | No/18,000 |
| 3 | 91.0 | No/19,000 |
| 4 | 94.8 | No/19,300 |
| 5 | 99.4 | No/20,500 |
| 6 | 104.7 | No/20,500 |
| 7 | 109.5 | No/23,700 |
| 8 | 115.1 | No/30,400 |
| ASTM Oil 438 Laboratory Reactor | | |
| 1 | 74.0 | No/16,570 |
| 2 | 101.0 | No/14,100 |
| 3 | 109.0 | No/21,120 |
| 4 | 113.0 | No/26,400 |
| 5 | 127.0 | No/30,000 |
| 6 | 133.0 | No/29,800 |
| 7 | 152.0 | No/27,300 |

TABLE II

Comparison of MRV TP-1 viscosity and Kinematic viscosity increase @ 40° Celsius from the Sequence IIIG and Laboratory Reactor Aged Oils

| Sample | % Viscosity Increase @ 40° Celsius | MRV TP-1 Ys, Pa/Viscosity, cP |
|---|---|---|
| ASTM Oil 435 Sequence IIIG Engine | | |
| 1 | 163.0 | Yes/84,800 |
| 2 | 168.0 | Yes/110,100 |
| 3 | 172.0 | Yes/84,500 |
| 4 | 176.0 | Yes/91,900 |
| 5 | 222.0 | Yes/300,200 |
| 6 | 230.0 | Yes/294,000 |
| 7 | 279.0 | Yes/210,700 |
| 8 | 305.0 | Yes/400,000 |
| ASTM Oil 435 Laboratory Reactor | | |
| 1 | 185.0 | Yes/99,300 |
| 2 | 226.0 | Yes/83,500 |
| 3 | 256.0 | Yes/182,800 |
| 4 | 310.0 | Yes/85,400 |

TABLE III

Comparison of MRV TP-1 viscosity and Kinematic viscosity increase @ 40° Celsius from the Sequence IIIG and Laboratory Reactor Aged Oils

| Sample | % Viscosity Increase @ 40° Celsius | MRV TP-1 Ys, Pa/Viscosity, cP |
|---|---|---|
| ASTM Oil 434 Sequence IIIG Engine | | |
| 1 | 63.0 | No/29,000 |
| 2 | 87.0 | No/34,200 |
| 3 | 90.0 | No/31,900 |
| 4 | 99.0 | No/45,600 |
| 5 | 127.0 | No/49,200 |
| 6 | 133.0 | No/48,900 |
| 7 | 250.0 | No/86,400 |
| ASTM Oil 434 Laboratory Reactor | | |
| 1 | 57.0 | No/30,000 |
| 2 | 59.0 | No/32,500 |

TABLE III-continued

Comparison of MRV TP-1 viscosity and Kinematic viscosity increase @ 40° Celsius from the Sequence IIIG and Laboratory Reactor Aged Oils

| Sample | % Viscosity Increase @ 40° Celsius | MRV TP-1 Ys, Pa/Viscosity, cP |
|---|---|---|
| 3 | 94.0 | No/43,300 |
| 4 | 118.0 | No/48,000 |
| 5 | 122.0 | No/57,600 |

The invention claimed is:

1. A method for the determination of the oxidative stability of a lubricating fluid, comprising:
   introducing a sample of the lubricating fluid under test in an reaction cell;
   introducing catalytic amounts of a catalyst to the reaction cell;
   heating the cell to the oxidation temperature of the lubricating fluid and maintaining this temperature;
   delivering a gas comprising oxygen at constant flow rate through the cell over the course of the reaction;
   delivering a gas comprising nitrogen dioxide at a constant flow rate through the cell for a specified time;
   applying and maintaining a specified vacuum on the reaction cell such that the reaction cell is maintained under a reduced pressure ranging from 0.05 to 0.07 MPa;
   allowing the mixture to react for a specified time;
   measuring the viscosity of the oxidized lubricating fluid.

2. The method according to claim 1 wherein the oxidation temperature is in the range of 160° C. to 180° C.

3. The method according to claim 1 wherein the specified time for allowing the mixture to react is in the range of 30 to 50 hours.

4. The method according to claim 1, wherein the nitrogen dioxide flow is in the range of 0.15 to 0.18 milliliters per hour over 11 to 13 hours.

5. The method according to claim 1, wherein the delivering of the gas is performed under a reduced pressure.

6. The method according to claim 1, wherein the total amount of nitrogen dioxide delivered to the reaction cell is in the range of 1 to 2% by weight based on the total amount of lubricating fluid at the start of the test.

7. The method according to claim 1, wherein the Mini-Rotary Viscosity of the lubricating fluid is measured according to ASTM D 4684.

8. The method according to claim 1, wherein the increase of the kinematic viscosity at 40° C. of the lubricating fluid is measured according to ASTM D 445.

9. The method according to claim 1, wherein the lubricating fluid is an engine oil lubricant or a transmission or a hydraulic fluid.

10. The method according to claim 1, wherein flow of the gas containing oxygen is in the range of 180 to 190 milliliters per minute throughout the reaction.

11. The method according to claim 10 wherein the reduced pressure of the specified vacuum is in the range of 0.061 to 0.063 MPa.

12. The method according to claim 1, wherein the heating of the cell is performed under a reduced pressure.

13. The method according to claim 12 wherein the reduced pressure of the specified vacuum is in the range of 0.061 to 0.063 MPa.

14. The method according to claim 12 wherein the reduced pressure of the specified vacuum is in the range of 0.057 to 0.064 MPa.

15. The method according to claim 1, wherein iron ferrocene is used as catalyst.

16. The method according to claim 15, wherein iron ferrocene is added to the reaction mixture at 10 to 20 ppm based on the lubricating fluid charge.

* * * * *